United States Patent [19]

Lawrence

[11] 4,110,319

[45] Aug. 29, 1978

[54] THIOCARBAMATE ADDITIVES FOR SULFUR VULCANIZABLE POLYMERS

[75] Inventor: John P. Lawrence, Stow, Ohio

[73] Assignee: The Goodyear Tire & Rubber Company, Akron, Ohio

[21] Appl. No.: 728,692

[22] Filed: Oct. 1, 1976

[51] Int. Cl.$^2$ ............................................. C08C 19/20
[52] U.S. Cl. ................................. 526/17; 260/453 R; 260/783; 260/239 BF; 260/784; 260/791; 526/19; 526/20; 526/21; 526/22; 526/23; 526/30; 526/31; 544/1
[58] Field of Search ...................... 260/79.5 A, 79.5 B, 260/79.5 C, 783, 784, 791

[56] References Cited

U.S. PATENT DOCUMENTS 3,790,534  2/1974  Gattuso ........................ 260/79.5 B

*Primary Examiner*—Christopher A. Henderson, Jr.
*Attorney, Agent, or Firm*—J. A. Rozmajzl

[57] ABSTRACT

Thiocarbamates such as N,N-oxydiethylenecarbamyl 1-dodecyl disulfide are used to affect the vulcanization characteristics of sulfur vulcanizable polymers by increasing the state of vulcanization and/or improving scorch resistance and/or increasing the rate of vulcanization.

8 Claims, No Drawings

THIOCARBAMATE ADDITIVES FOR SULFUR VULCANIZABLE POLYMERS

This invention relates to compounds which generally function to increase the state (degree) of vulcanization when used during the sulfur vulcanization of rubbers. This invention also relates to compounds which provide a vulcanizable polymer with balanced processing and vulcanization characteristics. In addition, it relates to compounds which retard vulcanization during the processing of vulcanizable rubbery compositions. It also relates to compounds which function as activators, that is, secondary accelerators in sulfur type vulcanization systems. It also relates to processes for increasing the state of vulcanization of sulfur vulcanizable rubbery compositions and either increasing scorch delay periods and/or increasing vulcanization rates. It also relates to the vulcanized products resulting therefrom.

BACKGROUND OF THE INVENTION

The physical properties of a vulcanized composition are related to its state of vulcanization. Often, as the state of vulcanization is increased, certain physical properties are improved. Rubber additives such as sulfur donors can be used therefore to increase the state of vulcanization or to permit the use of lesser amounts of free sulfur.

Scorching during the processing of rubber is due to the premature or insipient vulcanization which can occur during any of the steps involved in the processing of the rubber prior to the final vulcanization step or during storage between said processing steps. Whereas a properly compounded unscorched rubber formulation can be die extruded or sheeted smoothly from a calender without lumping, a scorched material often becomes wavy or lumpy after sheeting and must be discarded. It is therefore desirable that rubber additives be used which reduce scorching. Such compounds are commonly referred to as retarders. U.S. Pat. No. 3,790,534 describes premature vulcanization inhibitors.

It is often desirable to increase the rate at which rubbery compositions are vulcanized. Sulfur vulcanizable rubbery compositions containing free sulfur are made to vulcanize more rapidly by the addition of an accelerator compound. Often the accelerator compound is referred to as a primary accelerator and is used in combination with another accelerator called an activator or secondary accelerator which further increases the vulcanization rate.

It is an object of this invention to provide compounds which will increase the state of vulcanization of vulcanized rubber polymers as well as compounds which are secondary accelerators (activators) and/or retarders (scorch inhibitors). Another object of the present invention is to provide processes which will improve the scorch resistance and rate of vulcanization of vulcanizable rubbery polymers and also the state of vulcanization of sulfur vulcanized rubbers.

SUMMARY OF THE INVENTION

The objects of the present invention are accomplished by a sulfur vulcanizable combination of a sulfur vulcanizable rubber and at least one compound conforming to one of the following structural formulae.

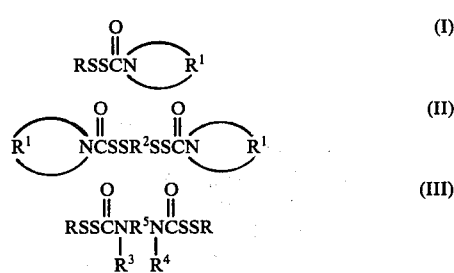

wherein R is selected from the group consisting of alkyl radicals (straight chain or branched) having 1 to 20 carbon atoms, monochloroalkyl radicals having 3 to 20 carbon atoms, cycloalkyl radicals having 5 to 10 carbon atoms, monochlorocycloalkyl radicals having 5 to 10 carbon atoms, aralkyl radicals having 7 to 11 carbon atoms (such as benzyl and phenylethyl) and aryl radicals having 6 to 10 carbon atoms, said aryl radicals optionally substituted with 1 or 2 radicals selected from the group consisting of alkyl radicals having 1 to 4 carbon atoms and the chloro radical. The symbol

denotes a heterocyclic amino radical selected from the group consisting of pyrrolidino, piperidino, hexamethylenimino, morpholino, 2,6-dimethylmorpholino, 2-methylpiperidino, 3-methylpiperidino, 4-methylpiperidino, 2,6-dimethylpiperidino, and 4-methylpiperazino. $R^2$ is selected from the group consisting of alkylene radicals (straight chain or branched) conforming to the following structural formula

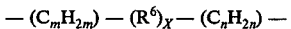

wherein X is 0 or 1, wherein $R^6$ is selected from the group consisting of —O—, —S— and phenylene, wherein when $R^4$ is phenylene or X is 0, $m$ and $n$ are positive whole numbers from 1 to 5, (e.g., $R^2$ can be 2,2'-oxydiethylene; 2,9-p-methyl; $\alpha,\alpha'$-p-xylyl, etc.) and arylene radicals having 6 to 10 carbon atoms, (e.g., $R^2$ can be p-phenylene, 1,4-naphthylene and 4,4'-biphenylene); $R^3$ and $R^4$ are selected from the group consisting of alkyl radicals (straight chain or branched) having 1 to 20 carbon atoms, cyclohexyl radical; aralkyl radicals having 7 to 12 carbon atoms (such as benzyl and phenylethyl) and aryl radicals having 6 to 10 carbon atoms; $R^5$ is selected from the group consisting of alkylene radicals (straight chain or branched) having 2 to 6 carbon atoms and p-phenylene and wherein $R^3$ and $R_4$ can be joined to constitute with the bridging $R^5$ group and the attached nitrogen atoms, a heterocyclic diamino radical selected from the group consisting of piperazino, 2,5-dimethylpiperazino, homopiperazino, and 4,4'-trimethylenedipiperidino. Preferably R is selected from the group consisting of ethyl, 1-propyl, 2-propyl, 1-butyl, 1-hexyl, 1-octyl, 1-dodecyl, cyclohexyl, benzyl, phenyl, 2-chlorocyclohexyl, 1-(2-chlorobutyl), 2-(1-chlorobutyl), 1-(2-chloropropyl), 2-(1-chloropropyl), 2-(3-chlorobutyl), and 2-(3-chloro-2,2,1-bicycloheptyl).

PREFERRED EMBODIMENTS

Preferably $R^3$ and $R^4$ are selected from the group consisting of methyl, ethyl, 1-propyl, 2-propyl, 1-butyl, cyclohexyl, benzyl and phenyl.

Preferably the

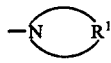

ring is morpholino or piperidino.

Preferably $R^2$ is selected from the group consisting of 1,2-ethylene, 1,2-propylene, 1,3-propylene, 1,4-tetramethylene, 1,6-hexamethylene, 1,8-octamethylene and 2,2'-oxydiethylene.

Preferably $R^5$ is selected from the group consisting of 1,2-ethylene, 1,3-propylene, and p-phenylene.

When $R^3$ and $R^4$ are joined with the two nitrogen atoms and the bridging group $R^5$, preferably the ring is selected from the group consisting of piperazino, 2,5-dimethylpiperazino, and 4,4'-trimethylenediperidino.

The following list of compounds is illustrative of those of type I.

| Retarder No. | |
|---|---|
| 1 | N,N-oxydiethylenecarbamyl 1-dodecyl disulfide |
| 2 | N,N-tetramethylenecarbamyl 1-dodecyl disulfide |
| 3 | N,N-pentamethylenecarbamyl 1-dodecyl disulfide |
| 4 | N,N-hexamethylenecarbamyl 1-dodecyl disulfide |
| 5 | N,N-oxydiethylenecarbamyl ethyl disulfide |
| 6 | N,N-oxydiethylenecarbamyl 1-propyl disulfide |
| 7 | N,N-oxydiethylenecarbamyl 2-propyl disulfide |
| 8 | N,N-oxydiethylenecarbamyl 1-butyl disulfide |
| 9 | N,N-oxydiethylenecarbamyl tert-butyl disulfide |
| 10 | N,N-oxydiethylenecarbamyl 1-hexyl disulfide |
| | N,N-oxydiethylenecarbamyl 1-octyl disulfide |
| 11 | N,N-oxydiethylenecarbamyl cyclohexyl disulfide |
| 12 | N,N-oxydiethylenecarbamyl benzyl disulfide |
| 13 | N,N-oxydiethylenecarbamyl phenyl disulfide |
| | N,N-oxydiethylenecarbamyl p-tolyl disulfide |
| | N,N-oxydiethylenecarbamyl p-chlorophenyl disulfide |
| 14 | N,N-oxydiethylenecarbamyl 2-chlorocyclohexyl disulfide |
| 16 | N,N-oxydiethylenecarbamyl 2-(3-chlorobutyl) disulfide |
| 18 | N,N-oxydiethylenecarbamyl 2-(3-chloro-2.2.1-bicycloheptyl disulfide |
| 24 | N,N-1,5-dimethylpentamethylenecarbamyl 1-dodecyl disulfide |
| 25 | N,N-3-methyliminodiethylenecarbamyl 1-dodecyl disulfide |
| 17 | The mixture N,N-oxydiethylenecarbamyl 1-(2-chloropropyl) disulfide and N,N-oxydiethylenecarbamyl 2-(1-chloropropyl) disulfide |
| 15 | The mixture N,N-oxydiethylenecarbamyl 1-(2-chlorobutyl) disulfide and N,N-oxydiethylenecarbamyl 2-(1-chlorobutyl) disulfide |

The following list of compounds is illustrative of those of Type II.

| Retarder No. | |
|---|---|
| 19 | 1,2-bis(N,N-oxydiethylenecarbamyldithio) ethane |
| 20 | 1,4-bis(N,N-oxydiethylenecarbamyldithio)-butane |
| | 1,6-bis(N,N-oxydiethylenecarbamyldithio)-hexane |
| 21 | 1,8-bis(N,N-oxydiethylenecarbamyldithio)-octane |
| | 2,2'-bis(N,N-oxydiethylenecarbamyldithio)-octane oxydiethane |
| | 1,2-bis(N,N-tetramethylenecarbamyldithio)-propane |
| | α, α'-bis(N,N-oxydiethylenecarbamyldithio)-p-xylene |
| | 2,9-bis(N,N-pentamethylenecarbamyldithio)-p-menthane |
| | 1,4-bis(N,N-oxydiethylenecarbamyldithio)-benzene |
| | 4,4'-bis(N,N-hexamethylenecarbamyldithio)-oxybisbenzene |
| | 4,4'-bis(N,N-oxydiethylenecarbamyldithio)-biphenyl |
| | 1,4-bis(N,N-oxydiethylenecarbamyldithio)-naphthalene |

The following list of compounds is illustrative of those of Type III.

| Retarder No. | |
|---|---|
| 22 | 1,4-bis(1-dodecyldithiocarbonyl)-piperazine |
| 23 | N,N'-bis(1-dodecyldithiocarbonyl)-4,4'-trimethylenedipiperidine |
| | 1,4-bis(ethyldithiocarbonyl)-piperazine |
| | 1,4-bis(1-propyldithiocarbonyl)-2,5-dimethylpiperazine |
| | 1,4-bis(2-propyldithiocarbonyl)-piperazine |
| | 1,4-bis(cyclohexyldithiocarbonyl)-homopiperazine |
| | 1,4-bis(benzyldithiocarbonyl)-piperazine |
| | N,N'-bis(phenyldithiocarbonyl)-N,N'-dimethylethylenediamine |
| | N,N'-bis(1-octyldithiocarbonyl)-N,N'-dibenzylethylenediamine |
| | N,N'-bis(1-dodecyldithiocarbonyl)-N,N'-dimethyl-p-phenylenediamine |
| | N,N'-bis(1-butyldithiocarbonyl)-N,N'-dicyclohexylethylenediamine |
| | N,N'-bis(1-hexyldithiocarbonyl)-N,N'-diethyl-1,3-propylenediamine |

When used with a conventional primary accelerator the compounds of structural formulae (I), (II) and (III) provide a vulcanizable polymer with balanced processing and vulcanization characteristics. In many vulcanization systems they provide both improved scorch resistance and improved activation characteristics. In systems where they provide only improved scorch resistance or improved activation characteristics they do so without adversely affecting the scorch resistance or conversely the activation characteristics. This is unique in that conventional retarders normally adversely affect vulcanization rates, much less improve the rate, while conventional activators normally adversely affect scorch, much less improve scorch resistance. Whether these compounds act as both activators and retarders, just as an activator, or just as a retarder, is not only dependent upon the primary accelerator being used but also upon the particular polymer being vulcanized as well as the particular compound of the present invention being used. The effect of accelerator systems, polymeric environment and different compounds is illustrated herein. It should be noted, however, that regardless of the accelerator system used or the particular polymer vulcanized, the compounds almost always act as retarders. In any case the thiocarbamates of the present invention will act at least as one of the following: an activator or a retarder.

All of the compounds of the present invention can be prepared by well known prior art methods. The method of preparation is not critical to the preformance of the compounds of the present invention. The following are guidelines which can be used in the preparation of compounds of the present invention and are not intended to be limiting.

Chlorocarbonylsulfenyl chloride (CCSC), U.S. Pat. No. 3,422,452, is reacted with a thiol to produce a chlorocarbonyl hydrocarbyl disulfide according to German Pat. No. 1,219,925. The disulfide is reacted with a secondary heterocyclic amine in the presence of an acid binding agent such as sodium carbonate to form a sulfenyl thiocarbamate of type I.

Where R is aryl the reaction of CCSC with aromatic thiols does not form the desired product. Rather, the method described in J. Amer. Chem Soc., 82 155 (1960) can be used. The sulfenyl thiocarbamates are thereby formed by reacting an arenesulfenyl chloride with a thionocarbamate.

Bis(sulfenyl thiocarbamates) type II can be prepared by reacting two mols of CCSC with one mol of dithiol to yield an intermediate bis(chlorocarbonyl disulfide) which is reacted with two mols of a secondary heterocyclic amine to produce the desired product.

The previously described chlorocarbonyl hydrocarbyl disulfide (2 mols) can be reacted with one mol of a di-secondary amine to provide the bis(sulfenylthiocarbamates) of type III.

The process described in the earlier recited J. Amer. Chem. Soc. article can be used to prepare class II compound where $R^2$ is arylene and class III compounds where R is aryl because of the previously described limitations in the CCSC method.

The thiocarbamates of the present invention can be used with any conventional compounding additive such as carbon black, zinc oxide, antidegradants and stearic acid. They can be used in a sulfurless system with an accelerator (a sulfur donor or otherwise), preferably a primary accelerator, or with a sulfur vulcanization agent in the presence of an accelerator. For the purposes of this invention, sulfur vulcanizing agent means elemental sulfur (free sulfur) or sulfur donating vulcanizing agents, for example, an amine disulfide of a polymeric polysulfide. Preferably the thiocarbamates are used with both a sulfur vulcanization agent, preferably free sulfur, and an accelerator, preferably a primary accelerator. The invention is applicable to vulcanization accelerators of various classes using conventional accelerator levels. Regardless of what accelerator is used the thiocarbamates will still normally act as retarders. For example, rubber mixes containing the aromatic thiazole accelerators which include N-cyclohexyl-2-benzothiazolesulfenamide, 2-mercaptobenzothiazole, N-tert-butyl-2-benzothiazolesulfenamide, 2-benzothiazolyl diethyldithiocarbamate and 2-(morpholinothio)-benzothiazole can be used. Other thiazole accelerators which may be used include 2-(aminodithio)-thiazoles and 2-(aminotrithio)-thiazoles such as 2-(morpholinodithio)-benzothiazole. Amine salts of mercaptobenzothiazole accelerators, for example, the t-butylamine salt mercaptobenzothiazole, and like salts of morpholine and 2,6-dimethylmorpholine can be used in the invention. Thiazole accelerators other than aromatic can be used. Stocks containing accelerators, for example, tetramethylthiuram disulfide, tetramethylthiuram monosulfide, alkehyde amine condensation products, thiocarbamylsulfenamides, thioureas, xanthates, and guanidine derivatives are substantially improved using the process of the present invention.

The thiocarbamates of the invention can be used in natural and synthetic rubbers and mixtures thereof. Synthetic rubbers that can be improved by the process of this invention include homopolymers and copolymers of dienes, both conjugated and nonconjugated, e.g., 1,3-dienes such as 1,3-butadiene and isoprene. Examples of such synthetic rubbers include neoprene (polychloroprene), cis-1,4-polybutadiene, cis-1,4-polyisoprene, butyl rubber, copolymers of 1,3-butadiene or isoprene with monomers such as styrene, acrylonitrile and methyl methacrylate. Ethylene/propylene terpolymers, for example ethylene/propylene/dicyclopentadiene terpolymers, also benefit from the practice of the present invention.

The thiocarbamates can be added to the rubbers by any conventional technique such as milling or Banburying.

All of the working examples herein are intended to illustrate but not limit the scope of the present invention. Unless indicated otherwise all parts are parts by weight.

The following examples illustrate the preparation of compounds of the present invention.

EXAMPLE 1

A solution of 6.2 grams (0.1 mol) of ethanthiol in 10 milliliters of hexane was added dropwise under nitrogen to a stirred solution of 13.1 grams (0.1 mol) of chlorocarbonylsulfenyl chloride in 15 milliliters of hexane. The temperature of the reaction was maintained at $-20°$ C. during the addition. The reaction mixture was then stirred one hour at room temperature and concentrated under reduced pressure. The resulting yellow liquid chlorocarbonyl ethyl disulfide was taken up in 100 milliliters of chloroform and added in one portion to a vigorously stirred mixture of 9.0 grams (0.1 mol) of morpholine, 12.0 grams of sodium carbonate, 50 milliliters of chloroform and 300 milliliters of water. The resulting mixture was stirred 15 minutes, the lower organic phase separated, dried ($Na_2SO_4$) and concentrated under reduced pressure to afford 20.5 grams (99.0 percent) of N,N-oxydiethylenecarbamyl ethyl disulfide as a white solid, melting point $50° - 51°$ C.

EXAMPLE 2

A solution of 4.7 grams (0.05 mol) of 1,2-ethanedithiol in 10 milliliters of chloroform was added dropwise under nitrogen to a stirred solution of 13.1 grams (0.10 mol) of chlorocarbonylsulfenyl chloride in 15 milliliters of chloroform at $-10°$ to $-15°$ C. The reaction mixture was stirred one hour at room temperature then concentrated under reduced pressure. The resulting pale yellow solid 1,2-bis(chlorocarbonyldithio)-ethane was taken up in 100 milliliters of chloroform and added in one portion to a vigorously stirred mixture of 9.0 grams (0.1 mol) of morpholine, 12.0 grams of sodium carbonate, 50 milliliters of chloroform and 30 milliliters of water. The resulting mixture was stirred 20 minutes at room temperature, the lower organic layer separated, dried ($Na_2SO_4$) and concentrated under reduced pressure to give 17.2 grams (89.6 percent) of 1,2-bis(N,N-oxydiethylene-carbamyldithio)ethane as a white solid, melting point $184° - 186°$ C.

EXAMPLE 3

A solution of 101 grams (0.5 mol) of 1-dodecanethiol in 50 milliliters of hexane was added dropwise under nitrogen to a stirred solution of 65.5 grams (0.5 mol) of chlorocarbonylsulfenyl chloride in 75 milliliters of hexane at $-10°$ to $-20°$ C. The mixture was stirred 2 hours at room temperature then concentrated under reduced pressure to yield 148 grams (99.8 percent) of pale yellow liquid chlorocarbonyl 1-dodecyl disulfide.

15.0 grams (0.05 mol) of chlorocarbonyl 1-dodecyl disulfide was dissolved in 50 milliliters of chloroform and added in one portion to a vigorously stirred mixture of 2.2 grams (0.025 mol) of piperazine, 6.0 grams of sodium carbonate, 25 milliliters of chloroform and 150 milliliters of water. After 15 minutes the lower organic layer was separated, dried ($Na_2SO_4$) and concentrated under reduced pressure to afford 12.3 grams (81.2 percent) of white solid 1,4-bis(1-dodecyldithiocarbonyl)-piperazine, melting point $106° - 108°$ C.

EXAMPLE 4

A solution of 8.2 grams (0.1 mol) of cyclohexene in 15 milliliters of dichloromethane was added dropwise under nitrogen to a stirred solution of 26.2 grams (0.2 mol) of chlorocarbonylsulfenyl chloride in 25 milliliters of dichloromethane at −20° C. The reaction mixture was allowed to warm to room temperature and then concentrated under reduced pressure to afford 22.9 grams (93.5 percent) of colorless liquid chlorocarbonyl 2-chlorocyclohexyl disulfide. The product was taken up in 50 milliliters of chloroform and added in one portion to a vigorously stirred mixture of 9.0 grams (0.1 mol) of morpholine, 12.0 grams of sodium carbonate, 50 milliliters of chloroform and 200 milliliters of water. The mixture was stirred 15 minutes then the lower organic layer was separated, dried ($Na_2SO_4$) and concentrated under reduced pressure to yield 27.6 grams (100 percent) of colorless liquid N,N-oxydiethylenecarbamyl 2-chlorocyclohexyl disulfide.

EXAMPLE 5

3.4 grams (0.025 mol) of sulfuryl chloride was added dropwise to a stirred and refluxing solution of 5.5 grams (0.025 mol) of phenyl disulfide in 50 milliliters of benzene under nitrogen. After 30 minutes the red solution of benzene sulfenyl chloride was cooled to room temperature and added dropwise to a stirred solution of 8.75 grams (0.05 mol) of O-ethyl N,N-oxydiethylenethioncarbamate in 25 milliliters of benzene. After the mildly exothermic reaction had subsided the reaction mixture was stirred for 80 minutes then concentrated under reduced pressure to afford 12.8 grams (100 percent) of N,N-oxydiethylenecarbamyl phenyl disulfide as a yellow liquid.

Compounds of the present invention were evaluated in Stocks A through G which are described below.

TABLE I

| Base Stock Compositions and Cure Data | |
|---|---|
| Base Stock A | Parts by Weight |
| Natural rubber | 100.00 |
| HAF black | 50.00 |
| Zinc oxide | 3.00 |
| Stearic acid | 3.00 |
| Paraffinic oil | 3.00 |
| Sulfur | 2.50 |
| Wing Stay 100 | 1.00 |
| 2-(morpholinothio)-benzothiazole | 0.50 |
| Base Stock B | |
| Same as A with the exception that 0.5 part of N-cyclohexyl-2-benzothiazole-sulfenamide was used in place of 2-(morpholinothio)-benzothiazole. | |
| Base Stock C | |
| Same as A with the exception that 0.5 part of 2-(morpholinodithio)-benzothiazole was used in place of 2-(morpholinothio)-benzothiazole. | |
| Base Stock D | |
| Same as C with the exception that 0.75 part of resorcinol and 1.5 parts of hexamethylenetetramine were added to the formulation. | |

TABLE II

| Base Stock E | Parts by Weight |
|---|---|
| SBR 1712 | 137.50 |
| ISAF black | 68.00 |
| Zinc oxide | 5.00 |
| Stearic acid | 1.50 |
| Sulfur | 1.50 |
| 2-(morpholinodithio)-benzothiazole | 1.00 |
| Base Stock F | |
| Same as E with the exception that 0.5 part of N-cyclohexyl-2-benzothiazole-sulfenamide was used in place of 2-(morpholinodithio)-benzothiazole. | |
| Base Stock G | |
| Same as E with the exception that 1.0 part of benzothiazyl disulfide and 0.75 part of diphenylguanidine were used in place of 2-(morpholinodithio)-benzothiazole. | |

A Monsanto Oscillating Disk Rheometer (275° F., 3° arc, 120 minute motor, low mode) was used to obtain the following measurements on Stock A using various compounds of the present invention.

$\Delta Rh$ = maximum torque minus minimum torque in inch pounds which is a measure of the degree or state of vulcanization (crosslinking).

$t_2$ = time in minutes for a 2 inch pound rise in torque above the minimum (Rheometer scorch).

$t_{90}$ = time in minutes to reach 90 percent crosslinking.

$t_{90}$-$t_4$ = measure of rate of cure in minutes. The Mooney scorch data were obtained according to ASTM D-1646 at 270° F.

$T\Delta 5$ = time in minutes for a 5 point rise above the minimum viscosity.

The data obtained using various compounds in Stock A are listed in Table III.

TABLE III

| Evaluation of Retarders in Base Stock A | | | | | | |
|---|---|---|---|---|---|---|
| Compound No. | Pts. by Wt. | $\Delta Rh$ | $t_2$ | $t_{90}$ | $t_{90}$-$t_4$ | $T\Delta 5$ |
| Control | — | 58.8 | 14.8 | 57.0 | 38.3 | 12.9 |
| 1 | 0.87 | 67.6 | 26.8 | 57.8 | 28.4 | 19.0 |
| 3 | 0.86 | 69.3 | 25.7 | 55.5 | 27.2 | 18.5 |
| Control | — | 63.1 | 12.7 | 54.8 | 38.7 | 11.7 |
| 2 | 0.83 | 71.0 | 18.5 | 48.3 | 27.0 | 15.7 |
| 4 | 0.90 | 72.6 | 18.8 | 49.5 | 28.4 | 14.9 |
| 24 | 0.93 | 68.9 | 22.2 | 52.0 | 27.8 | 17.8 |
| 25 | 0.90 | 71.0 | 20.5 | 50.5 | 28.2 | 16.0 |
| Control | — | 63.5 | 13.8 | 57.1 | 39.5 | 12.7 |
| 5 | 0.52 | 65.5 | 26.6 | 57.3 | 28.3 | 16.7 |
| 6 | 0.55 | 68.5 | 23.6 | 56.3 | 29.7 | 17.5 |
| 7 | 0.55 | 62.0 | 29.0 | 61.0 | 28.3 | 21.7 |
| 8 | 0.59 | 64.4 | 26.0 | 57.4 | 28.8 | 17.9 |
| 9 | 0.59 | 59.7 | 17.5 | 72.0 | 50.6 | 14.3 |
| 10 | 0.66 | 67.8 | 24.8 | 57.0 | 29.9 | 18.4 |
| 11 | 0.65 | 66.9 | 25.6 | 60.5 | 31.1 | 20.6 |
| 12 | 0.67 | 67.0 | 23.0 | 56.3 | 31.2 | 16.6 |
| Control | — | 60.5 | 15.5 | 59.3 | 39.7 | 12.9 |
| 13 | 0.50 | 63.4 | 20.8 | 53.2 | 31.4 | 16.7 |
| Control | — | 57.6 | 11.9 | 54.1 | 38.9 | 13.6 |
| 14 | 0.74 | 63.2 | 18.5 | 55.5 | 33.5 | 18.3 |
| 15 | 0.67 | 62.0 | 19.3 | 59.8 | 37.6 | 16.9 |
| 16 | 0.67 | 64.9 | 18.1 | 57.2 | 35.6 | 16.2 |
| 17 | 0.64 | 60.6 | 16.7 | 56.2 | 37.1 | 15.5 |
| 18 | 0.77 | 63.5 | 22.1 | 60.4 | 33.7 | 20.9 |
| Control | — | 64.9 | 15.1 | 56.1 | 37.3 | 12.3 |
| 19 | 0.77 | 73.3 | 19.3 | 48.8 | 27.7 | 12.5 |
| 20 | 0.82 | 71.9 | 20.0 | 49.1 | 26.6 | 13.5 |
| 21 | 0.94 | 75.0 | 17.2 | 46.1 | 26.8 | 11.8 |
| 22 | 1.21 | 67.0 | 23.1 | 56.0 | 30.9 | 18.5 |
| 23 | 1.46 | 69.5 | 21.8 | 59.6 | 35.3 | 16.5 |

All of the above compounds acted as activators and retarders with the exception of Compound No. 9, which acted solely as a retarder.

Compounds No. 1 and No. 7 were evaluated in Stocks B, C, D, E. F and G.

In Stocks B and C each acted as an activator and a retarder.

In Stock D each acted as a retarder.

In Stocks E and F both acted as activators and retarders.

In Stock G each acted as an activator.

A comparison was made between cyclohexyl-N,N-dicyclohexylcarbamyl disulfide, a compound of U.S. Pat. No. 3,790,534 and isopropyl-N,N-oxydiethylenecarbamyl disulfide in the formation described in Table I of the aforementioned patent. The scorch properties of the stocks were determined with a larger rotor Mooney viscometer at 250° F. times to 5 point and 20 point rises were measured. The compounds were used at the 0.5 part level. The results are listed below.

| Retarder | Mooney Scorch | |
|---|---|---|
| | 5 point | 20 point |
| Isopropyl-N,N-oxydiethylenecarbamyl disulfide | 23.0 | 25.4 |
| Cyclohexyl-N,N-dicyclohexylcarbamyl disulfide | 18.5 | 20.1 |
| None | 17.7 | 19.3 |

The compound derived from the heterocyclic amine (morpholine) was the superior retarder.

The above examples are not intended to be limiting, but rather illustrative. Any of the retarders, accelerators and rubbers described earlier herein can be substituted in the preceding examples. In addition the levels of the retarders and other components in said examples could be altered in accordance with the general teachings herein.

The additives of this invention can be used at various concentrations as low as 0.25 part per 100 parts by weight of rubber, and even as low as 0.10 or even 0.05 part. Conventional levels would frequently be 0.5 and 1.0 part although levels as high as 1.5, 3.0, 5.0 and even 10 parts can be used. Most frequently the concentration ranges from 0.25 to 5.0 parts, more preferably from 0.25 to 3.0 parts, and most preferably from 0.25 to 1.50 parts.

The compounds of the present invention are preferably added to the rubbery polymer at the same time that the accelerator is added, although this order of addition is not necessary to the successful utilization of the compounds of this invention.

The compounds of the present invention are effective in the presence of organic accelerators whether they are diarylguanidines such as diphenylguanidine, or thiazoles more specifically benzothiazyl amino disulfides, such as 2-(morpholinodithio)-benzothiazole, or thiazoles (also sulfenamides), more specifically thiazolesulfenamides, and even more specifically benzothiazolesulfenamides such as 2-(morpholinothio)-benzothiazole and N-cyclohexyl-2-benzothiazolesulfenamide, i.e., regardless of what type of organic accelerator is used. Thiuram sulfides such as tetramethylthiuram monosulfide and disulfide and tetraethyl thiuram monosulfide and disulfide may also be used as well as other benzothiazolesulfenamides such as N-(t-butyl)-2-benzothiazolesulfenamide.

Various organic accelerators useful within the practice of this invention are described and illustrated in the *Vanderbilt Rubber Handbook*, 1968 Edition, R. T. Vanderbilt Company, Inc., particularly at pages 242 and 244 and also in the bulletin of the Elastomer Chemicals Dept. of the E. I. du Pont de Nemours and Co. (inc.) entitled, "Accelerators, Vulcanizing Agents and Retarders, Brochure No. SD A54457".

The polymers in which the thiocarbamates of the present invention are incorporated remain suitable for their art recognized uses, e.g., in tires and industrial products.

Compounds referred to earlier herein as being retarders and/or activators in natural rubber and SBR are merely illustrative and not limiting.

The balanced processing and vulcanization characteristics are most often obtained when free sulfur (elemental sulfur) and a primary accelerator are used with the thiocarbamate.

Sometimes compounds are both a sulfur donor (and therefore a sulfur vulcanizing agent) and an accelerator, e.g., 2-(morpholinodithio)-benzothiazole. Such compounds can be used with the thiocarbamates, with or without another sulfur vulcanizing agent and/or another accelerator.

The compounds of the present invention can be used effectively in any sulfur vulcanizable polymer and with any organic accelerating agent.

When $R^6$ is —O— or —S—, $m$ and $n$ are positive whole numbers from 2 to 5.

While certain representative embodiments and details have been shown for the purpose of illustrating the invention it will be apparent to those skilled in this art that various changes and modifications may be made therein without departing from the spirit or scope of the invention.

What I claim is:

1. A sulfur vulcanizable diene polymer selected from the group consisting of natural rubber and synthetic diene polymers prepared from a monomer system containing diene monomer, said sulfur vulcanizable diene polymer having incorporated therein at least one thiocarbamate having the following structural formula

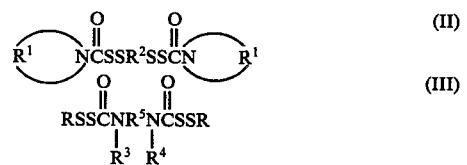

wherein R is selected from the group consisting of alkyl radicals having 1 to 20 carbon atoms, monochloroalkyl radicals having 3 to 20 carbon atoms, cycloalkyl radicals having 5 to 10 carbon atoms, monochlorocycloalkyl radicals having 5 to 10 carbon atoms, aralkyl radicals having 7 to 11 carbon atoms and aryl radicals having 6 to 10 carbon atoms, said aryl radicals optionally substituted with 1 or 2 radicals selected from the group consisting of alkyl radicals having 1 to 4 carbon atoms and the chloro radical, wherein the symbol

denotes a heterocyclic amino radical selected from the group consisting of pyrrolidino, piperidino, hexamethyleneimino, morpholino, 2,6-dimethylmorpholino, 2-methylpiperidino, 3-methylpiperidino, 4-methylpiperidino, 2,6-dimethylpiperidino, and 4-methylpiperazino, $R^2$ is selected from the group consisting of alkylene radicals conforming to the following structural formula

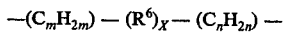

and arylene radicals having 6 to 10 carbon atoms, wherein X is 0 or 1, wherein $R^6$ is selected from the group consisting of —O—, —S— and phenylene, wherein when $R^6$ is phenylene or X is 0, $m$ and $n$ are positive whole numbers from 1 to 5 and wherein when $R^6$ is —O— or —S—, $m$ and $n$ are positive whole numbers from 2 to 5; $R^3$ and $R^4$ are selected from the group consisting of alkyl radicals having 1 to 20 carbon atoms, cyclohexyl radical; aralkyl radicals having 7 to 12 carbon atoms and aryl radicals having 6 to 10 carbon atoms; $R^5$ is selected from the group consisting of alkylene radicals having 2 to 6 carbon atoms and p-phenylene and wherein $R^3$ and $R^4$ can be joined to constitute with the bridging $R^5$ group and the attached nitrogen atoms, a heterocyclic diamino radical selected from the group consisting of piperazino, 2,5-dimethylpiperazino, homopiperazino, and 4,4'-trimethylenediperidino.

2. The sulfur vulcanizable diene polymer according to claim 1 wherein R is selected from the group consisting of ethyl, 1-propyl, 2-propyl, 1-butyl, 1-hexyl, 1-octyl, 1-dodecyl, cyclohexyl, benzyl, phenyl, 2-chlorocyclohexyl, 1-(2-chlorobutyl), 2-(1-chlorobutyl), 1-(2-chloropropyl), 2-(1-chloropropyl), 2-(3-chlorobutyl), and 2-(3-chloro-2,2,1-bicycloheptyl, $R^3$ and $R^4$ are selected from the group consisting of methyl, ethyl, 1-propyl, 2-propyl, 1-butyl, cyclohexyl, benzyl and phenyl, the

ring is morpholino or piperidino, $R^2$ is selected from the group consisting of 1,2-ethylene, 1,2-propylene, 1,3-tetramethylene, 1,6-hexamethylene, 1,8-octamethylene and 2,2'-oxydiethylene, $R^5$ is selected from the group consisting of 1,2-ethylene, 1,3-propylene and p-phenylene, and when $R^3$ and $R^4$ are joined with the two nitrogen atoms and the bridging group $R^5$ the ring is selected from the group consisting of piperazino, 2,5-dimethylpiperazino and 4,4'-trimethylenediperidino.

3. The sulfur vulcanizable diene polymer according to claim 1 wherein the polymer has incorporated therein an organic accelerating agent.

4. The sulfur vulcanizable diene polymer according to claim 1 wherein the polymer has incorporated therein a sulfur vulcanizing agent.

5. The sulfur vulcanizable diene polymer according to claim 3 wherein the organic accelerating agent is a primary accelerator and the polymer has incorporated therein elemental sulfur.

6. The sulfur vulcanizable diene polymer according to claim 1 wherein the thiocarbamate is present in the amount of from 0.25 part to 5.0 parts by weight per 100 parts by weight of polymer.

7. The sulfur vulcanizable diene polymer according to claim 1 wherein the polymer is selected from the group consisting of natural rubber, polychloroprene, cis-1,4-polybutadiene, cis-1,4 polyisoprene, butyl rubber, copolymers of butadiene and styrene, copolymers of butadiene and acrylonitrile and terpolymers of ethylene, propylene and dicyclopentadiene.

8. The sulfur vulcanizable diene polymer according to claim 1 wherein the group

is morpholino.

* * * * *